United States Patent [19]

Lester

[11] 4,365,709

[45] Dec. 28, 1982

[54] COMBINATION GAUZE PACKAGE AND GAUZE SPONGE DISPENSER

[76] Inventor: Thomas R. Lester, 105 Valencia Ct. N., Plant City, Fla. 33566

[21] Appl. No.: 266,375

[22] Filed: Sep. 18, 1981

[51] Int. Cl.$^3$ .......................... B65D 83/08; B65D 5/70
[52] U.S. Cl. .................... 206/362; 206/44 R; 206/494; 206/627; 229/7 R; 312/42
[58] Field of Search ............ 206/494, 499, 362, 44 R, 206/44.12, 627; 229/7 R; 221/34; 312/42

[56] References Cited

U.S. PATENT DOCUMENTS

| | | | |
|---|---|---|---|
| 1,186,706 | 6/1916 | Swift | 206/499 |
| 1,658,085 | 2/1928 | Hudson | 206/494 |
| 1,791,344 | 2/1931 | Bendheim | 229/7 R |
| 3,127,991 | 4/1964 | Burnett | 206/44 R |
| 3,520,401 | 7/1970 | Richter et al. | 206/362 |
| 3,580,472 | 5/1971 | Stawski | 206/499 |

*Primary Examiner*—William T. Dixson, Jr.
*Attorney, Agent, or Firm*—Arthur W. Fisher, III

[57] ABSTRACT

A combination gauze package and gauze sponge dispenser for storing and dispensing singly a plurality of gauze sponges, the gauze package comprising a elongated substantially rectangular package for retaining a plurality of gauze sponges in stacked array including a preformed tear portion comprising a top portion and a side portion with an opening tab and the gauze sponge dispenser comprising a hollow elongated substantially rectangular body vertically supported by means of a base wherein the gauze sponge dispenser is correspondingly configured to the gauze package to receive the gauze package therein, the hollow elongated substantially rectangular body including a slot formed on one vertical side thereof in registry with the side portion of the preformed tear portion such that a fully closed gauze package is inserted into the top of the gauze sponge dispenser and the preformed tear portion is removed along the side and top portions partially exposing the plurality of stacked array of gauze sponges to permit the serial removal of the uppermost gauze sponge from the gauze sponge dispenser.

6 Claims, 2 Drawing Figures

COMBINATION GAUZE PACKAGE AND GAUZE SPONGE DISPENSER

BACKGROUND OF THE INVENTION

1. Field of the Invention

A combination gauze package and gauze sponge dispenser for storing and dispensing a plurality of vertically stacked array of gauze sponges.

2. Description of the Prior Art

Gauze sponges are generally packaged and stored in bulk. When used in clinical laboratories, blood banks, physicians and dental offices as well as research and commercial laboratories, it is necessary to keep the individual sponges in a relatively sterile atmosphere. Thus it is desirable to provide means for singly or serially dispensing individual gauze sponges from the bulk and in addition eliminate lint, reduce waste and provide ease in distribution. To this end, the applicant has combined a unique combination of sponge package and dispenser.

SUMMARY OF THE INVENTION

The present invention relates to a combination gauze package and gauze sponge dispenser for storing and dispensing singly a plurality of gauze sponges. The gauze package comprises an elongated package constructed of paper or the like for retaining a plurality of gauze sponges in stacked array. The elongated package includes a preformed tear portion in combination with an opening tab.

The gauze sponge dispenser comprises a hollow elongated body vertically supported on a base. An elongated slot is formed on the front of the hollow elongated body.

In use, a fully closed gauze package is inserted into the top of the gauze sponge dispenser and the preformed tear portion is removed by means of the tab along the side and top portions thereof exposing the plurality of stacked array of gauze sponges to permit the serially removement of the uppermost gause sponge from the gauze sponge dispenser.

The invention accordingly comprises the features of construction, combination of elements, and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be had to the following detailed description taken in connection with the accompanying drawings in which.

Similar reference characters refer to similar parts throughout the several views of the drawings.

DETAILED DESCRIPTION OF THE PREFERRED EMBODIMENT

Figure 1:
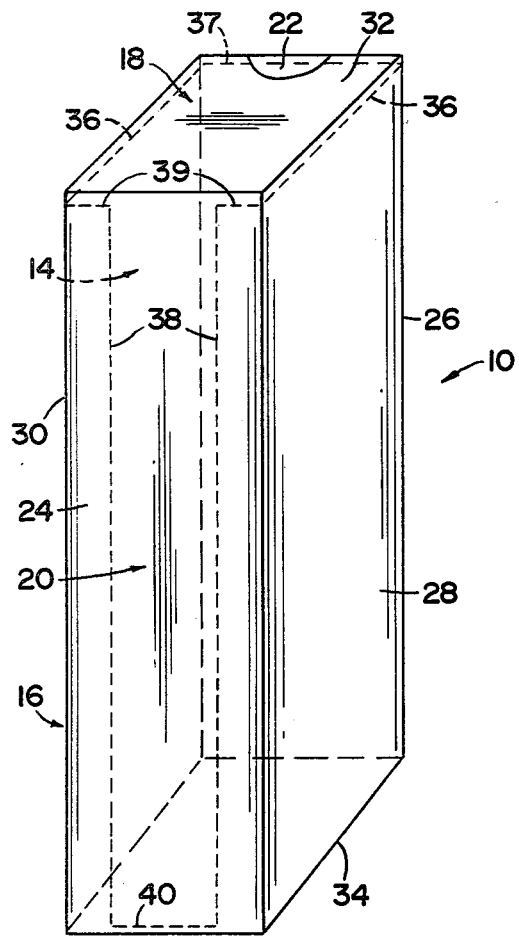
FIG. 1 is a detailed view of the gauze sponge dispenser.
Figure 2:
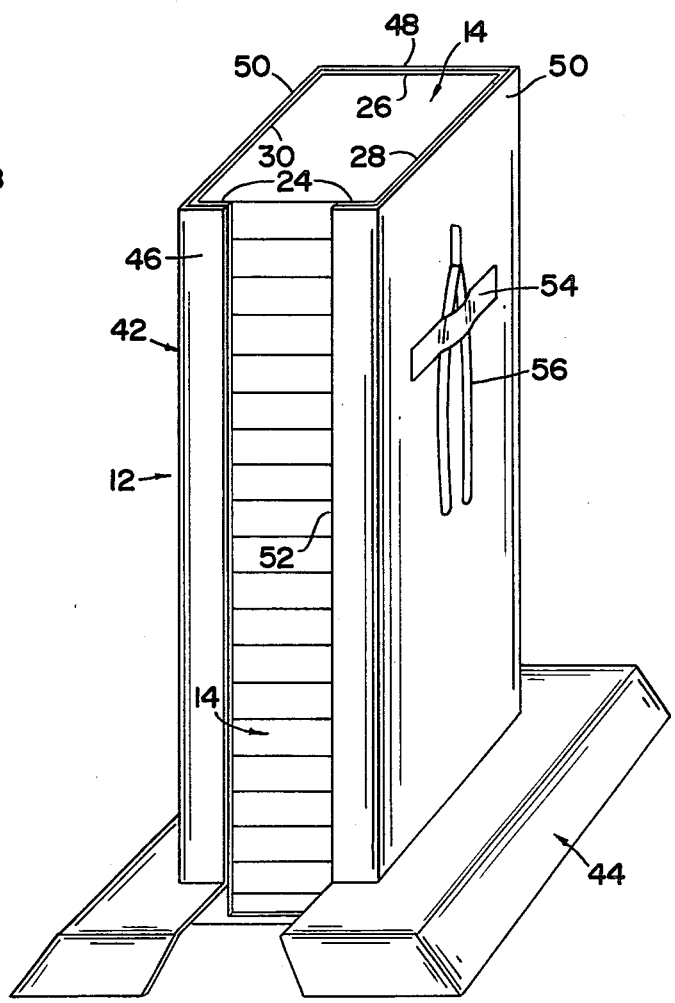
FIG. 2 is a detailed view of the gauze package.

As shown in FIGS. 1 and 2 the present invention relates to a combination gauze package and gauze sponge dispenser generally indicated as 10 and 12 respectively for storing and dispensing singly a plurality of gauze sponges each indicated as 14. The gauze package 10 comprises an elongated substantially rectangular package 16 constructed of paper or the like for retaining a plurality of gauze sponges 14 in stacked array. The elongated substantially rectangular package 16 includes a preformed tear portion comprising a top tear portion 18 and a front tear portion 20 in combination with an opening tab 22. The elongated substantially rectangular package 16 comprises a front and rear element 24 and 26 respectively in spaced relationship relative to each other by two side elements 28 and 30 respectively in combination with a top and bottom element 32 and 34 respectively. The top tear portion 18 is formed by a side tear lines 36 formed in the upper portion of side elements 28 and 30, rear tear line 37 or rear element 26 and interrupted tear line 39 front element 24. The side tear portion is formed by a tear lines 38 extending vertically on the front element 24 and interconnected by a tear line 40 extending across the bottom of the front element 24.

The gauze sponge dispenser 12 comprises a hollow elongated substantially rectangular body 42 vertically supported on a base 44. The hollow elongated substantially rectangular body 42 comprises front and rear element 46 and 48 respectively in spaced relationship relative to each other by side walls 50. An elongated slot 52 is formed on the front element 46. An opening is formed in the base 44 adjacent the lower end of the slot 52 to permit access to the lowermost gauze sponges 14 for removal as more specifically described hereinafter. Further, a forcep holder 54 is attached to side 50 to receive forceps 56. In use, a fully closed gauze package 10 is inserted into the top of the gauze sponge dispenser 12 and the preformed tear portion is removed by means of tab 22 along the front and top tear portions 20 and 18 respectively exposing the plurality of stacked array of gauze sponges 14 to permit the serially removement of the uppermost gauze sponge 14 from the gauze sponge dispenser 12. As shown, the front tear portion 20 is aligned in registry with the elongated slot 52. If desired the forceps 56 may be used by removing them from the holding 54.

It will thus be seen that the objects set forth above, and those made apparent from the preceding description are efficiently attained and since certain changes may be made in the above construction without departing from the scope of the invention, it is intended that all matter contained in the above description or shown in the accompanying drawings shall be interpreted as illustrative and not in a limiting sense.

It is also to be understood that the following claim are intended to cover all of the generic and specific features of the invention herein described, and all statements of the scope of the invention which as a matter of language, might be said to fall therebetween.

Now that the invention has been described,

What is claimed is:

1. A combination gauze package and gauze sponge dispenser for storing and dispensing singly a plurality of gauze sponges, said gauze package comprising an elongated package for retaining a plurality of gauze sponges in stacked array including a preformed tear portion, said preferomed tear portion comprises a top tear portion substantially horizontal plan and a front tear portion in a substantially vertical plane intersecting said top tear portion, and said gauze sponge dispenser comprising a hollow elongated body vertically supported on a base wherein said gauze sponge dispenser is correspondingly configured to said gauze package to receive said gauze package therein, said hollow elongated body including a slot formed on one vertical side thereof in registry with a portion of said preformed tear portion, said base including an opening formed therein adjacent the lower end of said slot such that a fully closed gauze package is inserted into said gauze sponge dispenser and said preformed tear portion is removed along the side and top portions partially exposing the plurality of stacked array of gauze sponges to permit the serial removal of the uppermost gauze sponge from the top of said gauze sponge dispenser.

2. The combination gauze package and gauze sponge dispenser as in claim 1 wherein said elongated package comprises a substantially rectangular configuration and said hollow elongated body comprises a substantially rectangular configuration.

3. The combination gauze package and gauze sponge dispenser as in claim 1 wherein said elongated package comprises a front and rear element in spaced relation relative to each other by a pair of side elements in combination with a top and bottom element.

4. The combination gauze package and gauze sponge dispenser as in claim 3 wherein top tear portion comprises a side tear lines formed in the upper portion of said side elements of said gauze package and a rear tear line formed in said rear element and an interrupted tear line formed on said front element of said gauze package.

5. The combination gauze package and gauze sponge dispenser as in claim 4 wherein said tear portion is formed by tear lines extending vertically on said front element interconnecting said bottom tear line extending across the lower portion of said front element.

6. The combination gauze package and gauze sponge dispenser as in claim 4 wherein said top tear portion further includes a tab disposed on the rear portion thereof.

* * * * *